US011478316B2

(12) United States Patent
Jiang et al.

(10) Patent No.: US 11,478,316 B2
(45) Date of Patent: Oct. 25, 2022

(54) SURGICAL ROBOT SYSTEM

(71) Applicant: Shanghai Microport Medbot (Group) Co., Ltd., Shanghai (CN)

(72) Inventors: Yizhi Jiang, Shanghai (CN); Yunlei Shi, Shanghai (CN); Yuyuan He, Shanghai (CN); Xiang Zhu, Shanghai (CN); Shuai Yuan, Shanghai (CN); Chao He, Shanghai (CN)

(73) Assignee: SHANGHAI MICROPORT MEDBOT (GROUP) CO., LTD., Shanghai (CN)

( * ) Notice: Subject to any disclaimer, the term of this patent is extended or adjusted under 35 U.S.C. 154(b) by 398 days.

(21) Appl. No.: 16/646,779

(22) PCT Filed: Aug. 3, 2018

(86) PCT No.: PCT/CN2018/098500
§ 371 (c)(1),
(2) Date: Mar. 12, 2020

(87) PCT Pub. No.: WO2019/056871
PCT Pub. Date: Mar. 28, 2019

(65) Prior Publication Data
US 2020/0289227 A1  Sep. 17, 2020

(30) Foreign Application Priority Data

Sep. 20, 2017  (CN) .......................... 201710854319.4
Sep. 22, 2017  (CN) .......................... 201710865638.5

(51) Int. Cl.
*G09G 5/00* (2006.01)
*A61B 34/00* (2016.01)
(Continued)

(52) U.S. Cl.
CPC .............. *A61B 34/71* (2016.02); *A61B 34/20* (2016.02); *A61B 34/37* (2016.02); *A61B 34/76* (2016.02);
(Continued)

(58) Field of Classification Search
CPC .......... A61B 17/34; A61B 2017/00477; A61B 2034/301; A61B 2034/302;
(Continued)

(56) References Cited

U.S. PATENT DOCUMENTS

| 6,037,927 A | 3/2000 | Rosenberg |
| 2007/0018958 A1 | 1/2007 | Tavakoli et al. |

(Continued)

FOREIGN PATENT DOCUMENTS

| CN | 101325920 A | 12/2006 |
| CN | 101528151 A | 9/2009 |

(Continued)

*Primary Examiner* — Insa Sadio
(74) *Attorney, Agent, or Firm* — Muncy, Geissler, Olds & Lowe, P.C.

(57) ABSTRACT

A surgical robot system includes a slave unit and a computing unit. The slave unit includes a robotic arm, a surgical instrument, a cannula and a sensing element. The robotic arm drives the surgical instrument to rotate about a remote center of motion (RCM). The cannula is detachably coupled to a terminal of the robotic arm and defines an axis passing through the RCM. The surgical instrument is detachably connected with the terminal of the robotic arm and extends distally through the cannula, and the sensing element is disposed on the cannula and senses an axial deformation of the cannula. The computing unit determines a radial force acting on the terminal of the surgical instrument, from a force on the cannula sensed by the sensing element, according to the principle of torque balance. This surgical robot system has force feedback capabilities and obtains the radial force acting on the terminal of the surgical instrument (Continued)

directly from a measurement with higher accuracy and not requiring any additional component, providing for reduced structural complexity of the surgical instrument.

15 Claims, 7 Drawing Sheets

(51) Int. Cl.
*A61B 34/20* (2016.01)
*A61B 34/37* (2016.01)
*B25J 13/08* (2006.01)
*A61B 34/30* (2016.01)

(52) U.S. Cl.
CPC ....... B25J 13/085 (2013.01); *A61B 2034/301* (2016.02)

(58) Field of Classification Search
CPC ........ A61B 2090/061; A61B 2090/065; A61B 34/20; A61B 34/37; A61B 34/71; A61B 34/76; B25J 13/085
See application file for complete search history.

(56) References Cited

U.S. PATENT DOCUMENTS

| | | |
|---|---|---|
| 2013/0165869 A1 | 6/2013 | Blumenkranz et al. |
| 2013/0237995 A1 | 9/2013 | Lee et al. |
| 2015/0223832 A1* | 8/2015 | Swaney ................. A61B 34/10 703/1 |
| 2016/0216167 A1* | 7/2016 | Blumenkranz ........ A61B 34/30 |

FOREIGN PATENT DOCUMENTS

| | | |
|---|---|---|
| CN | 105407781 A | 3/2016 |
| CN | 108210078 A | 6/2018 |
| EP | 1015068 A1 | 7/2000 |
| EP | 1908428 A1 | 4/2008 |
| EP | 3179936 A1 | 6/2017 |
| JP | 2002159509 A | 6/2002 |
| JP | 2008289902 A | 12/2008 |
| JP | 2009522017 A | 6/2009 |
| JP | 2016019766 A | 2/2016 |
| JP | 2017522134 A | 8/2017 |
| WO | WO-9825666 A1 | 6/1998 |
| WO | WO-2016018815 A1 | 2/2016 |
| WO | WO2017020081 A1 | 2/2017 |

* cited by examiner

SURGICAL ROBOT SYSTEM

TECHNICAL FIELD

The present invention relates to the technical field of medical instruments and, more specifically, to a surgical robot system.

BACKGROUND

In common scenarios of surgical robot-assisted surgery, a surgeon operates a robot's master end located remotely from a patient and controls, in a master-slave control scheme, the motion of surgical instruments at the robot's slave end around surgical sites. The master end may be, but are not limited to, a series homogenous robotic arm, a series heterogeneous robotic arm, a parallel robotic arm, exoskeleton gloves and the like, which can control the position and orientation of the surgical instruments relative to the surgical sites.

In general, at the slave end, multiple robotic arms capable of holding surgical instruments and an endoscope are deployed. In these cases, it is very important to enable the surgeon to precisely perceive the results of interactions of the surgical instruments with the patient's tissue. In other words, it is necessary for the surgeon to obtain perceivable indications of forces applied by the surgical instruments, which are also the forces exerted by the body tissue to terminal of these surgical instruments.

Among existing surgical robot systems, the DaVinci system has been recognized as one of the most outstanding ones in the world. However, surgical instruments in such systems both in China and abroad, including the DaVinci system, are still suffering from a number of deficiencies, the major ones of which are as follows:

1. Some existing surgical robots are absent of force feedback mechanisms, leaving surgical instruments therein unable to feed back their operating environment and status during a surgical procedure. Consequently, the surgeon cannot perceive any interference from outside the field of vision encountered, or a touch with a certain body part, by any of the surgical instruments. This will significantly affect the surgeon's feeling of use and the outcome of the procedure or even lead to failure of the surgical procedure.

2. While there are some existing surgical robots with force feedback systems, such systems are associated with high computational and structural complexity and generally operate in an indirect manner in which additionally components are employed or measurements on transmission mechanisms are introduced for calculation of the forces acting on surgical instruments. This will lead to significant increases in the surgical instruments' mass and structural complexity. One example of such an indirect force feedback system is a trocar device for delivery of a surgical instrument disclosed in WO2005067804A. This device includes an annular force transducer disposed on an internal wall of the trocar, a cannula inserted in a central orifice of the force transducer and a surgical instrument that can pass through the cannula and protrude outside from a distal end of the trocar, coming into interaction with a target surgical site. The force transducer disposed between the trocar and cannula is intended to indirectly measure a force exerted by the surgical instrument on the target site. In one embodiment of that application, another annular force transducer is disposed where a proximal end of the surgical instrument is coupled to a robotic arm in order to facilitate the measurement on the force feedback. This device is overall complicated in structure and requires a complex force feedback algorithm.

SUMMARY OF THE DISCLOSURE

It is an objective of some embodiments of the present invention to overcome at least one of the problems of conventional mechanisms for measuring a contact force on a terminal of a surgical instrument, such as structural complexity, computational complexity and low accuracy, by providing a surgical robot system.

To this end, some embodiments of the present invention discloses a surgical robot system, comprising a slave unit and a computing unit, wherein the slave unit comprises a robotic arm, a surgical instrument, a cannula and a sensing element, wherein the robotic arm is configured to drive the surgical instrument to pivot about a remote center of motion, the cannula is detachably connected to a terminal of the robotic arm, and an axis of the cannula extends through the remote center of motion, the surgical instrument is detachably connected with the terminal of the robotic arm and extends distally through the cannula, the sensing element is disposed on the cannula and configured to sense an axial deformation of the cannula; the computing unit is configured to determine, according to a principle of torque balance, a radial force acting on the terminal of the surgical instrument based on a force acting on the cannula sensed and determined by the sensing element.

Optionally, a protrusion is provided on an inner wall of the cannula, and the protrusion is configured to be able to generate a point-contact when brought into contact with the surgical instrument, wherein the cannula comprises a reference point located at the remote center of motion, with the protrusion and sensing element both disposed on one side of the reference point farther away from the terminal of the robotic arm, and wherein the computing unit is configured to determine the radial force acting on the terminal of the surgical instrument based on a force acting on the cannula at a location of the point-contact sensed and determined by the sensing element.

Optionally, one protrusion is provided on the inner wall of the cannula; or a plurality of protrusions are provided on and symmetrically distributed across the inner wall of the cannula.

Optionally, the sensing element is disposed to be closer to the terminal of the robotic arm than the protrusion is disposed to be.

Optionally, a plurality of sensing elements are symmetrically distributed on an inner surface and/or an outer surface of the cannula.

Optionally, the cannula comprises a mount configured to detachably connect with the terminal of the robotic arm.

Optionally, the cannula is configured to be coaxial or in a clearance fit with the surgical instrument.

Optionally, the surgical instrument comprises a power module, an instrument shaft, a first characteristic point, a second characteristic point and a third characteristic point; the power module is connected to a proximal end of the instrument shaft, the instrument shaft is configured to be able to generate a point-contact when brought into contact with the cannula, the first characteristic point is defined at a location where the instrument shaft is connected to the power module, the second characteristic point is defined at a location of the instrument shaft in correspondence with a terminal of the cannula, the third characteristic point is defined at the terminal of the surgical instrument, and wherein the radial force acting on the third characteristic point is determinable by the computing unit based on a force acting on the second characteristic point, a distance between the first characteristic point and the second characteristic point and a distance between the first characteristic point and the third characteristic point.

Optionally, the surgical instrument comprises a power module, an instrument shaft, a first characteristic point, a second characteristic point and a third characteristic point; the power module is connected to a proximal end of the instrument shaft, the instrument shaft is configured to be able to generate a point-contact when brought into contact with the protrusion, the first characteristic point is defined at a location where the instrument shaft is connected to the power module, the second characteristic point is defined at a location where the protrusion is contactable with the instrument shaft, the third characteristic point is defined at the terminal of the surgical instrument, and wherein the radial force acting on the third characteristic point is determinable by the computing unit based on a force acting on the second characteristic point, a distance between the first characteristic point and the second characteristic point and a distance between the first characteristic point and the third characteristic point.

Optionally, the distance between the first characteristic point and the second characteristic point is obtained based on an initial value of the distance between the first characteristic point and the second characteristic point determined during initialization of the surgical robot system and a displacement of the surgical instrument along an axis of the cannula from an initial position of the surgical instrument determined during the initialization of the surgical robot system.

Optionally, the surgical instrument comprises a power module and a transmission mechanism configured to transfer an output force from the power module to the terminal of the surgical instrument, the power module comprising an axial drive motor configured to drive the surgical instrument to move axially, and wherein the computing unit is configured to determine an axial force acting on the terminal of the surgical instrument based on an output force from the axial drive motor and a reduction ratio of the transmission mechanism.

Optionally, the output force from the axial drive motor is computable from an electric current flowing through the axial drive motor or measureable by a sensor disposed on an output shaft of the axial drive motor.

Optionally, a coating is provided on an outer surface of the surgical instrument, to reduce a friction between the surgical instrument and the cannula.

Optionally, the surgical robot system further comprises a master unit comprising a force indicator configured to enable the radial force acting on the terminal of the surgical instrument to be perceived.

Optionally the force indicator is a master manipulator provided with a motor communicatively connected to the computing unit, or the force indicator is an imaging system.

In summary, some embodiments of the present invention provide a surgical robot system including a slave unit and a computing unit. The slave unit includes a robotic arm, a surgical instrument, a cannula and a sensing element. The sensing element is disposed on the cannula and configured to sense an axial deformation of the cannula, and the computing unit is configured to determine a contact force exerted on the cannula from the sensed axial deformation, as well as a radial force acting on a terminal of the surgical instrument according to the contact force. In the other embodiments, a protrusion is disposed on an inner wall of the cannula, which is configured to be able to come into point-contact with the surgical instrument, and the computing unit is configured to determine the radial force acting on the terminal of the surgical instrument based on a point-contact force exerted on the cannula according to the axial deformation sensed by the sensing element. When an external force acts on the terminal of the surgical instrument, the surgical instrument will deform and come into contact with the cannula. In response, the cannula will exert a supporting force on the contacted portion of the surgical instrument. A moment of the supporting force is balanced by that of a radial component (i.e., the aforementioned radial force) of the external force acting on the terminal of the surgical instrument. Therefore, the radial force on the terminal of the surgical instrument can be accurately and uniquely determined by measuring the contact force between the cannula and the surgical instrument, while avoiding measurement errors that may arise from variation in the structure of the surgical instrument's terminal. In particular, since the cannula is provided with the protrusion that can be brought into point-contact with the surgical instrument, the radial force acting on the terminal of the surgical instrument can be determined with even higher accuracy by measuring a contact force between the protrusion and the surgical instrument.

Compared with the conventional solutions using a motor output to calculate the force acting on the terminal of the surgical instrument, the surgical robot system of the present invention is advantageous in both a simpler force transmission path and higher radial force measurement accuracy. Moreover, the radial force acting on the terminal of the surgical instrument can be obtained in an easier manner without requiring additional components, providing for lower structural complexity of the surgical instrument and facilitating its assembly. Further, since minor changes are required in the surgical instrument, various existing surgical instruments can be suitably used in the surgical robot system proposed by the present invention.

In these figures,

1 denotes a patient cart; 2 denotes a robotic arm; 3 denotes a surgical instrument; 301 denotes a power module; 302 denotes an instrument shaft; 303 denotes a terminal effector; 4 denotes an endoscope; 5 denotes a stereo imaging system;

6 denotes a master manipulator; 7 denotes an armrest; 8 denotes a patient; 10 denotes a computing unit;

9 denotes a cannula; 901 denotes a mount; 902 denotes a protrusion; and 903 denotes a sensing element.

DETAILED DESCRIPTION

The above and other objectives, features and advantages of the present invention will become more apparent from the following detailed description of the proposed surgical robot system, which is to be read in connection with FIGS. 1 through 7. Note that the figures are much simplified and may not be drawn to scale, and the sole purpose of them is to facilitate easy and clear explanation of the disclosed embodiments. As used herein, a "trailing end", "terminal" or "distal end" refers to an end farther way from an operator and closer to a patient, while a "leading", "leading end" or "proximal" refers to an end closer to the operator and farther way from the patient.

Figure 1:
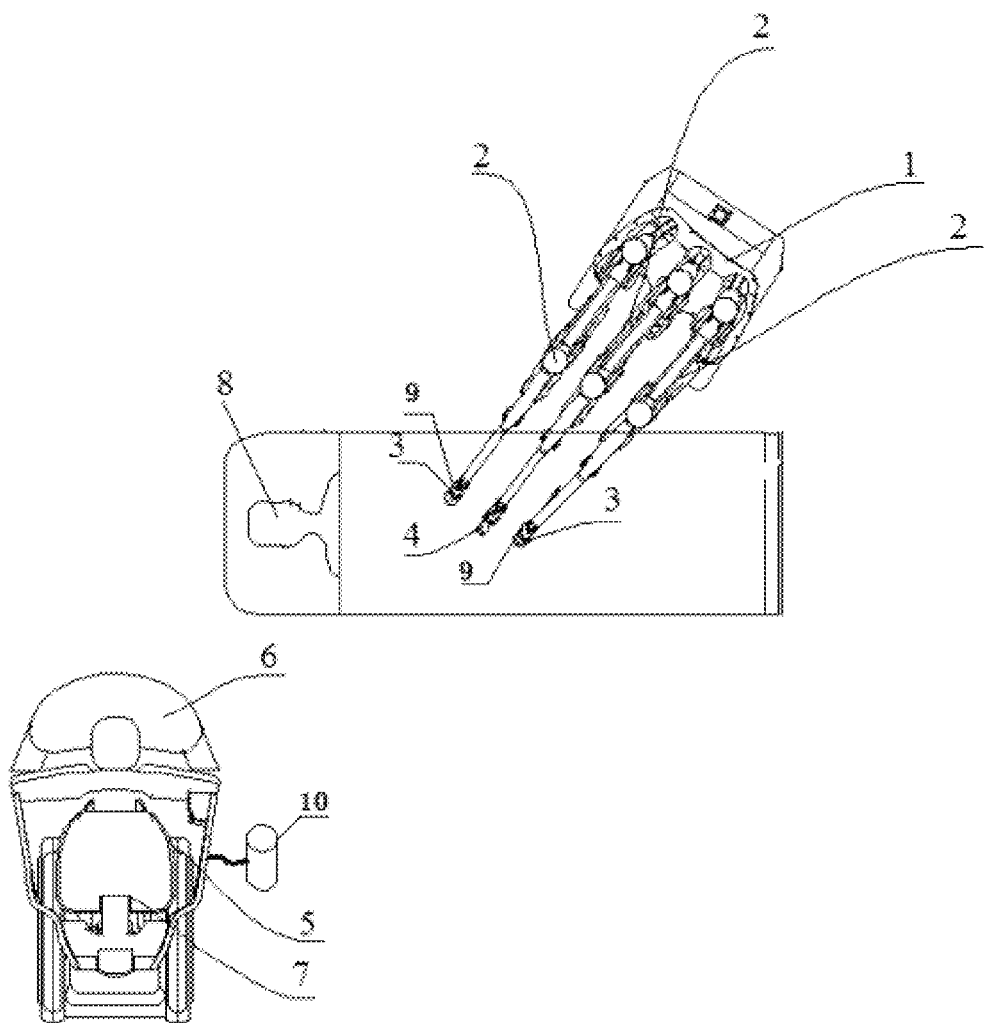
FIG. 1 is a structural schematic of a surgical robot system according to an embodiment of the invention.

FIG. 1 is a structural schematic of a surgical robot system according to an embodiment of the invention. The surgical robot system includes a slave unit including a patient cart 1, a robotic arm 2, a surgical instrument 3, an endoscope 4 and a cannula 9. As a base of the whole slave unit, the patient cart 1 supports all the mechanical mechanisms. Meanwhile, the patient cart 1 is moveable on the ground to allow the slave unit to approach or leave a patient 8.

The robotic arm 2 with multiple degrees of freedom is mounted on the patient cart 1 and configured to drive the surgical instrument 3 to pivot about a remote center of motion (RCM). When the patient cart 1 moves into the vicinity of the patient 8, the robotic arm 2 may be adjusted so that the surgical instrument 3 reaches a predetermined target surgical site. That is, the RCM is located around the surgical site by adjusting both the patient cart 1 and the robotic arm 2. The surgical instrument 3 is mounted at a terminal of the robotic arm 2, either fixedly or movably. As an effector of the slave unit, the surgical instrument 3 will eventually enter into the patient's body at the surgical site so as to treat a target lesion in vivo. During a whole surgical procedure, the surgical instrument 3 will move with multiple degrees of freedom around the RCM, and in order to prevent the movements of the surgical instrument 3 from causing damage to the body's surface tissue and to create a sealed environment within the body, the cannula 9 is disposed between the surgical instrument 3 and said surface tissue. The cannula 9 is detachably connected with a terminal of the robotic arm 2 and defines an axis passing through the RCM. One end of the surgical instrument 3 is detachably connected to the terminal of the robotic arm 2, and the other end is inserted through the cannula 9 and distally into the patient's body so as to approach the lesion. In this way, the surgical instrument 3 can move in synchronization with the cannula 9 around the RCM, while also being able to achieve movement along and/or rotation about the axis thereof within the cannula 9.

The endoscope 4 is mounted at a terminal of a different robotic arm 2 from that on which the surgical instrument 3 is installed and is configured to collect image information about the surgical environment. The image information may include, but is not limited to, information about tissue around the lesion and that about a posture and position of the surgical instrument 3. When mounted on the robotic arm 2, the endoscope 4 may be communicatively connected to the master unit as detailed below so as to enable real-time display of the information about the surgical environment collected thereby. The endoscope 4 may be three-dimensional or not, which is not limited by the present invention.

As shown in FIG. 1, the surgical robot system may further include a master unit including an imaging system 5, a master manipulator 6 and an armrest 7. During a surgical procedure, with the information from the endoscope 4 being displayed by the imaging system 5, a surgeon can monitor motion of the surgical instrument 3 in real time, and accordingly control the subsequent movement of the surgical instrument 3 by manipulating the master manipulator 6. The surgeon may sit at a surgical console and, with the aid of the imaging system 5, observe the position and motion of the terminal of the surgical instrument within the patient's body. Based on the observations, the surgeon can control a subsequent movement of the terminal by manipulating the master manipulator 6, thus allowing for a minimally invasive operation. As a result of the manipulation of the master manipulator 6 by the surgeon, the surgical instrument 3 may make movements in multi-dimensional space, as required in the surgical procedure, such as pitching, yawing, rotating, opening and closing. The armrest 7 can support the surgeon's arm so that the surgeon can maintain a higher comfort when the surgical procedure lasts for a long time. In addition, the armrest 7 can be raised and lowered to meet various needs of different surgeons.

The surgical robot system further includes a computing unit 10 communicatively connected to both the master and slave units, for example, by wired or wireless connections. The computing unit 10 is responsible for, based on a control strategy, processing sensor data and calculating various data required in the controlling. The computing unit 10 may determine a force acting on the cannula 9 from data transmitted by a sensing element 903 (e.g., strain and stress data) and thus determine a force acting on the terminal of the surgical instrument 3, and then transmit information about the force on the terminal of the surgical instrument 3 to a force indicator of the master unit, so that the force on the terminal of the surgical instrument 3 can be known. The force indicator may be the imaging system 5, which can display the magnitude and direction of the force on the terminal of the surgical instrument 3.

Alternatively, the force indicator may be the master manipulator 6 equipped with a motor. While the surgeon is operating the system, the computing unit 10 may control the motor of the master manipulator 6 based on the information about the force on the terminal of the surgical instrument 3 and may exert a force acting onto the surgeon. Apparently, the control made from the master manipulator 6 to the surgical instrument 3 is basic to the master/slave control loop in the surgical robot system. In order to better simulate the actual circumstances of a surgical procedure, i.e., simulate the force acting on the surgical instrument 3 during the procedure, it is desired that the surgical instrument 3 is able to feed back any force acting on it to the master manipulator 6, i.e., providing the surgical instrument 3 with force feedback capabilities. After a force acting on the cannula 9 is determined from the data sensed by the sensing element 903 (e.g., strain and stress data) and accordingly a force acting on the terminal of the surgical instrument 3 is determined from the force on the cannula 9, the computing unit 10 can issue a torque command to the motor of the master manipulator 6, to enable the operator to perceive the force acting on the terminal of the surgical instrument 3. More preferably, the master manipulator 6 may be provided with a vibrator. In this case, when the force on the terminal of the surgical instrument 3, which is determined from the data sensed by the sensing element 903 (e.g., strain and stress data), exceeds a preset threshold, the computing unit 10 can issue a vibration command to the vibrator of the master manipulator 6, notifying the operator about the excessive force on the terminal of the surgical instrument 3.

The surgical robot system according to this embodiment is able to measure a radial force on the terminal of the surgical instrument 3, i.e., a force exerted along a direction perpendicular to an axis of the surgical instrument 3.

Figure 2:
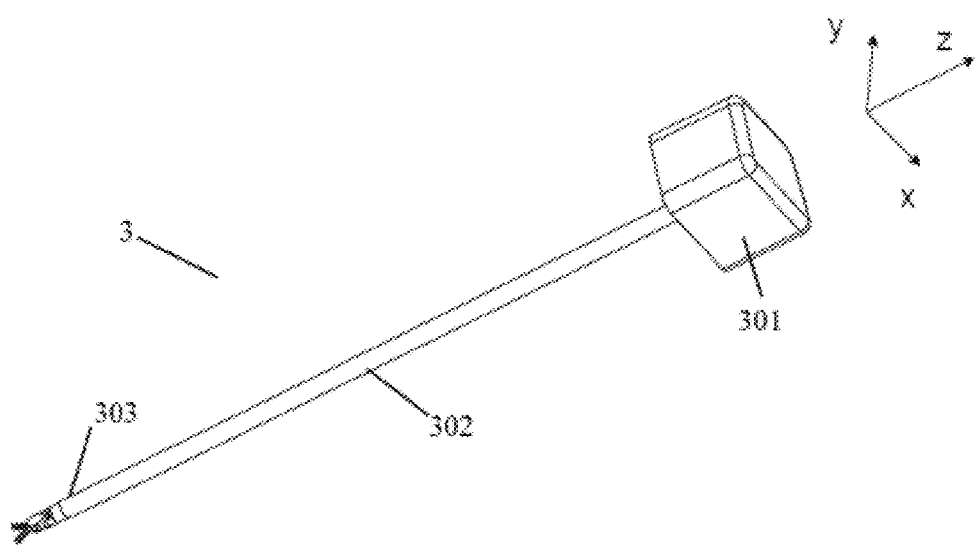
FIG. 2 is a structural schematic of a surgical instrument according to an embodiment of the invention.

FIG. 2 is a structural schematic of a surgical instrument according to an embodiment of the present invention. As shown, the surgical instrument 3 includes a power module 301, an instrument shaft 302, a force transmission mechanism and a terminal effector 303. The force transmission mechanism may for example employ wire transmission and be housed in the instrument shaft 302 and connected to both the power module 301 and terminal effector 303. The power module 301 is disposed at a leading end of the instrument shaft 302 (i.e., the end closer to the operator), while the terminal effector 303 is disposed at a terminal of the instrument shaft 302 (i.e., the end farther away from the operator). The power module 301 is configured to provide a driving force, which is transferred by the force transmission mechanism to the terminal effector 303, thus enabling the terminal effector 303 to perform a multi-dimensional rotational motion, an opening/closing action, etc. The terminal effector 303 is configured to perform actions, such as cutting, probing and pinching, to the patient's lesion. The present invention is not limited to any particular type of the terminal effector 303 as it can be scissors, pliers, a probe or the like.

Figure 3:
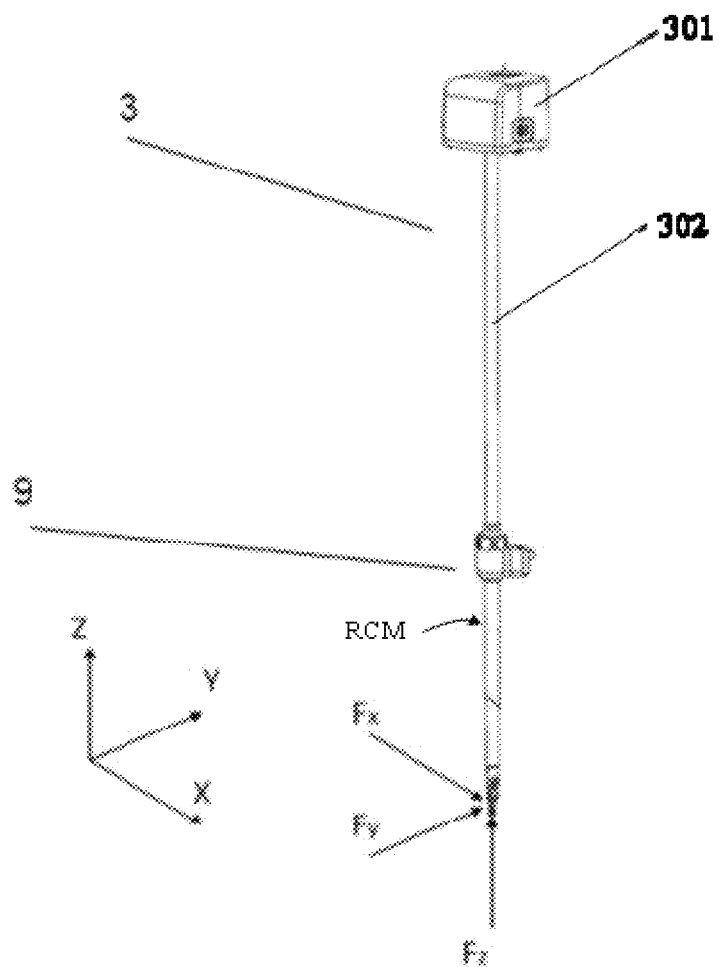
FIG. 3 schematically illustrates forces exerted by human tissue on a terminal of a surgical instrument that is inserted through a cannula, in accordance with an embodiment of the invention.

Additionally, in order to facilitate detection, a coordinate system may be defined for the surgical instrument 3. This coordinate system is not limited to the rectangular coordinate system as shown but can alternatively be a cylindrical coordinate system, a polar coordinate system or the like. With the illustrated rectangular coordinate system as an example, as shown in FIGS. 2 and 3, the coordinate system is established with three axes which are X axis, Y axis and Z axis, wherein the Z axis extends along an axis of the instrument shaft 302, X axis is perpendicular to the axis of the instrument shaft 302 and Y axis is determined according to the right-hand rule. In an actual surgical procedure, the terminal of the surgical instrument 3 (i.e., the end equipped with the terminal effector 303) will interact with the patient's tissue generally by applying thereto forces along the three axes. In response, according to Newton's third law of motion, the terminal of the surgical instrument 3 will be subject to the reaction forces which are equal in magnitude but opposite in direction to the acting force along the three axes, in which the reaction forces along the X and Y axes may be obtained by the sensing element 903 and computing unit 10. This will be described in greater detail below.

In the present embodiment, the power module 301 may be connected to a proximal end of the instrument shaft 302, and the instrument shaft 302 is received in the cannula 9. Preferably, the instrument shaft 302 may be configured to be able to come into point-contact with the cannula 9. Improved accuracy in radial force measurement at the terminal of the surgical instrument can be obtained by measuring a point-contact force between the cannula 9 and surgical instrument 3.

Figure 6:
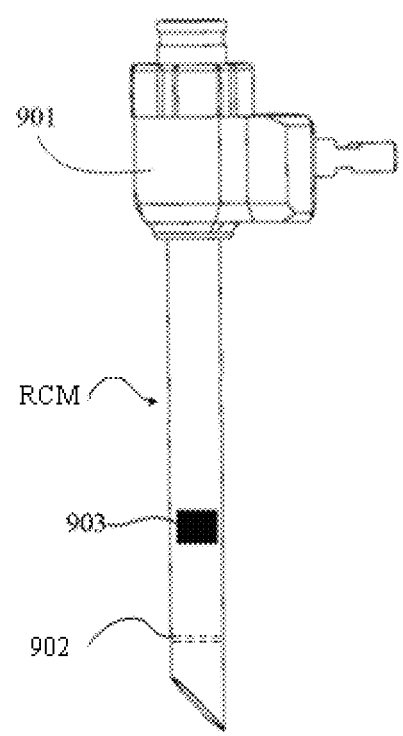
FIG. 6 is a structural schematic of a cannula according to an embodiment of the invention.

FIG. 6 is a structural schematic of a cannula (with a protrusion 902 therein, as indicated by dotted lines) according to an embodiment of the present invention. As shown in FIG. 6, the cannula 9 may include a mount 901 configured to be detachably connected with the terminal of the robotic arm 2. The cannula 9 may also include a protrusion 902 projecting from an inner wall of the cannula 9. The sensing element 903 may be attached on the cannula 9. Additionally, the cannula 9 may further include a reference point (not shown, fixed in position relative to the mount 901) located at the RCM. Both the protrusion 902 and sensing element 903 may be disposed on the side of the reference point farther away from the mount 901 (i.e., the side thereof farther away from the terminal of the robotic arm), and the protrusion 902 may be located even farther away than the sensing element 903 from the mount 901, i.e., from the terminal of the robotic arm.

During assembly, the instrument shaft 302 may be inserted through the cannula 9, with the protrusion 902 being configured to be able to come into point-contact with the instrument shaft 302. Preferably, the instrument shaft 302 is configured to be coaxial and in a clearance fit with the cannula 9. The sensing element 903 may be attached to either an inner surface or an outer surface of the cannula 9. Further, an end of the cannula 9 away from the mount 901 (i.e., the end on the same side as the protrusion 902 with respect to the reference point) may be tapered and able to puncture an object so as to diversify the functionality thereof.

Figure 4A:
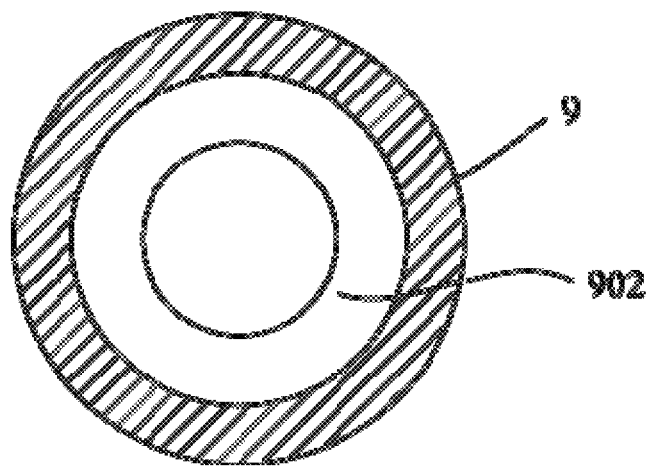
FIG. 4a is a transverse cross-sectional view of a cannula according to an embodiment of the invention.
Figure 4B:
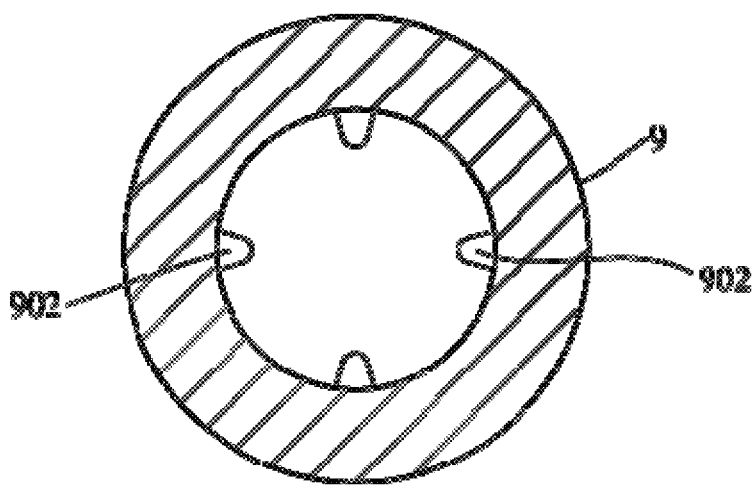
FIG. 4b is a transverse cross-sectional view of a cannula according to another embodiment of the invention.
Figure 4C:
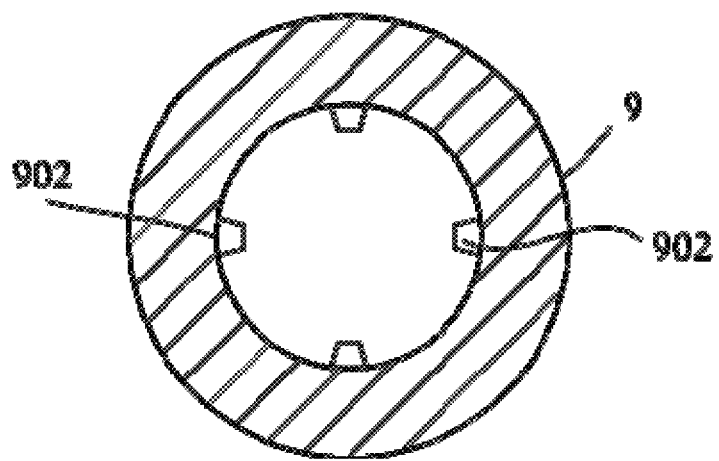
FIG. 4c is a transverse cross-sectional view of a cannula according to a still other embodiment of the invention.

In an embodiment, only one protrusion 902 may be provided, as shown in FIG. 4a, in the form of an annulus. In other embodiments, a plurality of such protrusions 902, for example, four protrusions 902, may be provided as shown in FIGS. 4b and 4c. Preferably, the protrusions 902 may be symmetrically distributed. However, the present invention is not limited to any particular number of protrusions 902.

The invention is also not limited to any particular shape of the protrusion(s) 902, as long as it is ensured that the instrument shaft 302 can come into point-contact with the cannula 9. Just for this reason, a width of each protrusion 902 along the circumferential direction of the instrument shaft 302 should be made as small as possible. As shown in FIG. 4b, in one embodiment, point-contact may occur between curved surface of the protrusions 902 and an outer surface of the instrument shaft 302. Alternatively, as shown in FIG. 4c, point-contact may occur between flat surfaces of the protrusions 902 and the outer surface of the instrument shaft 302 that is in the form of a circular rod.

Further, in order to ensure a more accurate measurement of an axial strain in the cannula 9, the sensing element 903 is preferably disposed to be closer to the mount 901 (i.e., closer to the terminal of the robotic arm) than the protrusion(s) 902 is disposed to be. For example, the sensing element 903 is disposed on a portion of the cannula between the reference point and protrusion(s) 902 (as shown in FIG. 6). Preferably, a plurality of (e.g., three or four) sensing elements 903 may be provided. More preferably, these sensing elements 903 may be symmetrically distributed. In the present embodiment, four sensing elements 903 may be provided, in which two are disposed along the X axis and in symmetry with each other with respect to the Y axis, and the other two are disposed along the Y axis and in symmetry with each other with respect to the X axis. Examples of devices that can be used as the sensing elements 903 may include, but not limited to, foil strain gauges, semiconductor resistive strain gauges, piezoelectric sensors, semiconductor pressure sensors, etc.

FIG. 3 schematically illustrates reaction forces applied by human tissue on the terminal of the surgical instrument that is inserted through the cannula, in accordance with an embodiment of the invention. As illustrated, when defining the direction from the terminal of the instrument shaft 302 to the leading end thereof as a positive (+) Z direction, the terminal of the surgical instrument 3 may receive a force $F_x$ in the +X direction, a force $F_y$ in the +Y direction and a force $F_z$ in the +Z direction, and the computing unit 10 is configured to determine the radial forces $F_x$ and $F_y$ or the resultant $F_{xy}$ thereof.

Under the effect of the forces acting on the terminal of the surgical instrument 3 in the three directions, the instrument shaft 302 may deform and come into contact with the protrusion 902 on the cannula 9, exerting thereon a contact force, which may be sensed by the sensing element 903 on the cannula 9. In addition, based on a relationship between a reaction force exerted by the cannula 9 on the instrument shaft 302 and the radial force(s) on the terminal of the surgical instrument, the radial force(s) ($F_x$ and $F_y$, or $F_{xy}$) may be calculated by the computing unit 10. Specifically, under the effect of the forces on the terminal of the surgical instrument 3, the instrument shaft 302 may deform and stop further deforming upon coming into point-contact with the protrusion 902. Meanwhile, the sensing element 903 will be stretched or compressed due to the axial deformation of the cannula 9 and hence sense the contact force applied by the instrument shaft 302 to the cannula 9, from which the reaction force $F_m$ from the cannula 9 (which is the resultant of a component $F_{mx}$ along the X axis and a component $F_{my}$ along the Y axis) can be determined.

Figure 5:
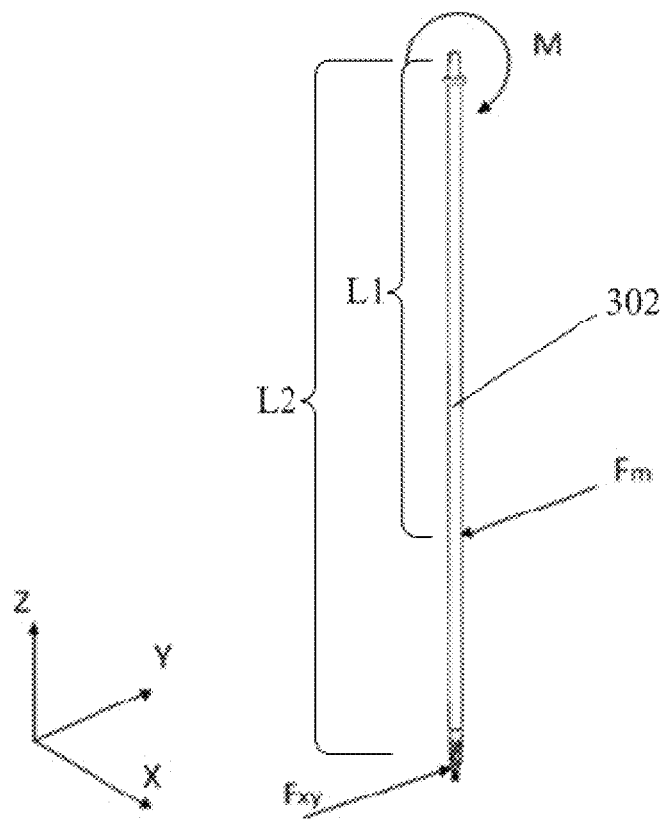
FIG. 5 schematically illustrates forces acting on a surgical instrument, in accordance with an embodiment of the invention.

The aforementioned relationship may be mathematically modeled using lengths from a first characteristic point defined at the proximal end of the instrument shaft 302 (i.e., where it is connected to the power module 301) respectively to a second characteristic point defined at a location of the instrument shaft 302 where it is contactable with the protrusion 902 and a third characteristic point defined at the terminal of the surgical instrument 3. As shown in FIG. 5, the length L1 from the first characteristic point to the second characteristic point and the length L2 from the first characteristic point to the third characteristic point may be both known beforehand. For example, the length L2 may be measured beforehand. However, since the length L1 will vary with the movement of the surgical instrument 3, it cannot be measured in advance. Nevertheless, an initial value $L1_s$ of the length L1 can be obtained during initialization of the surgical robot. A telescopic joint in the robotic arm 2 drives the surgical instrument 3 to move relative to the cannula 9 along the axis thereof, and the displacement sensor on the telescopic joint can measure in real time a displacement ΔL of the surgical instrument 3 from the initial position. As such, the length L1 can be determined in real time as $L1=L1_s+\Delta L$.

FIG. 5 schematically illustrates forces acting on the surgical instrument, in accordance with an embodiment of the invention. As shown, a moment M about the first characteristic point on the instrument shaft 302 should be zero as the resultant of:

(1) a moment of the radial force $F_{xy}$ acting on the third characteristic point about the first characteristic point, wherein the radial force $F_{xy}$ is the resultant of $F_x$ in the X axis and $F_y$ in the Y axis;

(2) a moment of the (resultant) reaction force $F_m$ acting on the second characteristic point about the first characteristic point; and (3) a support moment about the first characteristic point.

In practice, due to interaction between the cannula 9 and the instrument shaft 302 as well as the connection between the power module 301 and the instrument shaft 302, the support moment applied by the power module 301 to the instrument shaft 302 can be ignored. In addition, since $F_{xy}$ and $F_m$ are perpendicular to the axis of the instrument shaft 302 respectively, the moment of the radial force $F_{xy}$ about the first characteristic point, $F_{xy}L2$ is equal and opposite to the moment of the contact force $F_m$ about the first characteristic point, $F_mL1$. That is, $F_{xy}L2+F_mL1=0$, according to which the radial force $F_{xy}$ acting on the terminal can be calculated from the known parameters L1 and L2 and $F_m$ whose magnitude and direction can be measured by the sensing element 903. In other words, given the moment $F_{xy}L2$, which is the product of the radial force $F_{xy}$ and L2, is equal in magnitude and opposite in direction to the moment $F_mL1$, which is the product of the reaction force $F_m$ and L1, the radial force $F_{xy}$ can be given as:

$$F_{xy}=-\frac{F_mL1}{L2}$$

where, the minus sign denotes that its direction is opposite to that of the reaction force $F_m$.

The force $F_z$ acting on the terminal of the surgical instrument 3 in the Z axis (i.e., in the axial direction) may be determined otherwise. In one embodiment, the power module 301 may preferably include an axial drive motor for driving the surgical instrument 3 to move axially, and the computing unit 10 may be configured to determine the axial force $F_z$ on the terminal of the surgical instrument 3 based on an output force of the axial drive motor and a reduction ratio of the transmission mechanism. Here, the axial drive motor's output force may be calculated from a current follow in the motor or directly measured by a sensor disposed on an output shaft of the motor.

In order to avoid the signal interference resulting from the sliding friction caused by the instrument shaft 302 sliding in the cannula 9, a coating capable of reducing friction between the instrument shaft 302 and the protrusion 902 may preferably be provided over the outer surface of the instrument shaft 302. For example, the coating may be a Teflon coating, which can eliminate undesired signal interference resulting from the sliding friction, ensuring good accuracy in measuring the axial force.

Figure 7:
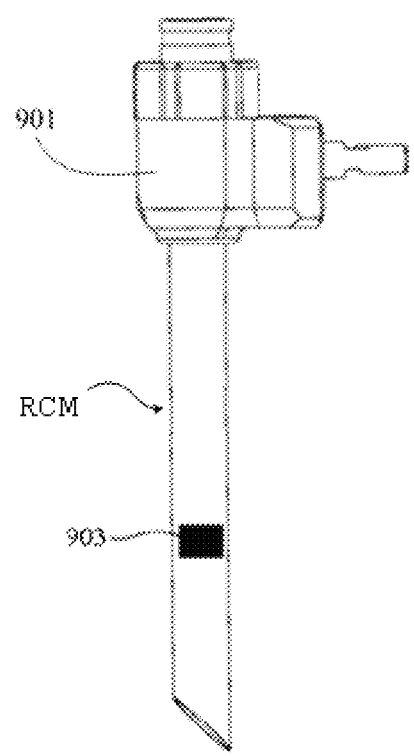
FIG. 7 is a structural schematic of a cannula according to another embodiment of the invention.

It is to be added that providing the protrusion(s) on the cannula 9 is merely a preferred embodiment of the invention, and those skilled in the art will recognize that even when the cannula 9 is a smooth structure without any protrusion disposed thereon, as shown in FIG. 7, the technical problem can also be solved and similar beneficial effects can also be obtained. In this case, the second characteristic point may be defined at the terminal of the cannula 9, and the radial force acting on the terminal of the surgical instrument can be calculated based on a length relationship accordingly derived from the principles and relationship described in supra in conjunction with the foregoing embodiments.

While a detail description has been given above of how forces acting on the terminal of the surgical instrument are measured and calculated, it is a matter of course that the present invention includes, but is not limited to, the above-described measurement and calculation methods, and any and all modifications made thereto are intended to also fall within the scope of the invention. Those skilled in the art can make other embodiments in light of the teachings of the foregoing embodiments.

Further, the computing unit 10 may employ an existing PLC controller, microcomputer, microprocessor or the like, and one skilled in the art will understand how to implement such a selection based on the disclosure herein in combination with the common general knowledge in the art.

In summary, some embodiments of the present invention provides a surgical robot system including a slave unit and a computing unit. The slave unit includes a robotic arm, a surgical instrument, a cannula and a sensing element. The sensing element is disposed on the cannula and configured to sense an axial deformation of the cannula, and the computing unit is configured to determine a contact force exerted on the cannula from the sensed axial deformation, as well as a radial force acting on a terminal of the surgical instrument according to the contact force. In the other embodiments, a protrusion is disposed on an inner wall of the cannula, which is configured to be able to come into point-contact with the surgical instrument, and the computing unit is configured to determine the radial force acting on the terminal of the surgical instrument based on a point-contact force exerted on the cannula according to the axial deformation sensed by the sensing element. When an external force acts on the terminal of the surgical instrument, the surgical instrument will deform and come into contact with the cannula. In response, the cannula will exert a supporting force (i.e., the aforementioned reaction force) on the contacted portion of the surgical instrument. A moment of the supporting force is balanced by that of a radial component (i.e., the aforementioned radial force) of the external force acting on the terminal of the surgical instrument. Therefore, the radial force on the terminal of the surgical instrument can be accurately and uniquely determined by measuring the contact force exerted by the cannula on the surgical instrument, while avoiding errors that may arise from variation in the structure of the surgical instrument's terminal. In particular, since the cannula is provided with the protrusion that can be brought into point-contact with the surgical instrument, the radial force acting on the terminal of the surgical instrument can be determined with even higher accuracy by measuring a contact force between the protrusion and the surgical instrument.

Compared with the conventional solutions using a motor output to calculate the force acting on the terminal of the surgical instrument, the surgical robot system of the present invention is advantageous in both a simpler force transmission path and higher radial force measurement accuracy. Moreover, the radial force acting on the terminal of the surgical instrument can be obtained in an easier manner without requiring additional components, providing for lower structural complexity of the surgical instrument and facilitating its assembly. Further, since minor changes are required in the surgical instrument, various existing surgical instruments can be suitably used in the proposed surgical robot system.

The description presented above is merely that of a few preferred embodiments of the present invention and does not limit the scope thereof in any sense. Any and all changes and modifications made by those of ordinary skill in the art based on the above teachings fall within the scope as defined in the appended claims.

What is claimed is:

1. A surgical robot system, comprising a slave unit and a computing unit, wherein
the slave unit comprises a robotic arm, a surgical instrument, a cannula and a sensing element, wherein
the robotic arm is configured to drive the surgical instrument to pivot about a remote center of motion,
the cannula is detachably connected to a terminal of the robotic arm, and an axis of the cannula extends through the remote center of motion,
the surgical instrument is detachably connected with the terminal of the robotic arm and extends distally through the cannula,
the sensing element is disposed on the cannula and configured to sense an axial deformation of the cannula;
the computing unit is configured to determine, according to a principle of torque balance, a radial force acting on the terminal of the surgical instrument based on a force acting on the cannula sensed and determined by the sensing element.

2. The surgical robot system of claim 1, wherein a protrusion is provided on an inner wall of the cannula, and the protrusion is configured to be able to generate a point-contact when brought into contact with the surgical instrument, wherein the cannula comprises a reference point located at the remote center of motion, with the protrusion and sensing element both disposed on one side of the reference point farther away from the terminal of the robotic arm, and wherein the computing unit is configured to determine the radial force acting on the terminal of the surgical instrument based on a force acting on the cannula at a location of the point-contact sensed and determined by the sensing element.

3. The surgical robot system of claim 2, wherein one protrusion is provided on the inner wall of the cannula; or a plurality of protrusions are provided on and symmetrically distributed across the inner wall of the cannula.

4. The surgical robot system of claim 2, wherein the sensing element is disposed to be closer to the terminal of the robotic arm than the protrusion is disposed to be.

5. The surgical robot system of claim 1, wherein a plurality of sensing elements are symmetrically distributed on an inner surface and/or an outer surface of the cannula.

6. The surgical robot system of claim 1, wherein the cannula comprises a mount configured to detachably connect with the terminal of the robotic arm.

7. The surgical robot system of claim 1, wherein the cannula is configured to be coaxial or in a clearance fit with the surgical instrument.

8. The surgical robot system of claim 1, wherein the surgical instrument comprises a power module, an instrument shaft, a first characteristic point, a second characteristic point and a third characteristic point; the power module is connected to a proximal end of the instrument shaft, the instrument shaft is configured to be able to generate a point-contact when brought into contact with the cannula, the first characteristic point is defined at a location where the instrument shaft is connected to the power module, the second characteristic point is defined at a location of the instrument shaft in correspondence with a terminal of the cannula, the third characteristic point is defined at the terminal of the surgical instrument, and wherein the radial force acting on the third characteristic point is determinable by the computing unit based on a force acting on the second characteristic point, a distance between the first characteristic point and the second characteristic point and a distance between the first characteristic point and the third characteristic point.

9. The surgical robot system of claim 2, wherein the surgical instrument comprises a power module, an instrument shaft, a first characteristic point, a second characteristic point and a third characteristic point; the power module is connected to a proximal end of the instrument shaft, the instrument shaft is configured to be able to generate a point-contact when brought into contact with the protrusion, the first characteristic point is defined at a location where the instrument shaft is connected to the power module, the second characteristic point is defined at a location where the protrusion is contactable with the instrument shaft, the third characteristic point is defined at the terminal of the surgical instrument, and wherein the radial force acting on the third characteristic point is determinable by the computing unit based on a force acting on the second characteristic point, a distance between the first characteristic point and the second characteristic point and a distance between the first characteristic point and the third characteristic point.

10. The surgical robot system of claim 8, wherein the distance between the first characteristic point and the second characteristic point is obtained based on an initial value of the distance between the first characteristic point and the second characteristic point determined during initialization of the surgical robot system and a displacement of the surgical instrument along an axis of the cannula from an initial position of the surgical instrument determined during the initialization of the surgical robot system.

11. The surgical robot system of claim 1, wherein the surgical instrument comprises a power module and a transmission mechanism configured to transfer an output force from the power module to the terminal of the surgical instrument, the power module comprising an axial drive motor configured to drive the surgical instrument to move axially, and wherein the computing unit is configured to determine an axial force acting on the terminal of the surgical instrument based on an output force from the axial drive motor and a reduction ratio of the transmission mechanism.

12. The surgical robot system of claim 11, wherein the output force from the axial drive motor is computable from an electric current flowing through the axial drive motor or measureable by a sensor disposed on an output shaft of the axial drive motor.

13. The surgical robot system of claim 11, wherein a coating is provided on an outer surface of the surgical instrument, to reduce a friction between the surgical instrument and the cannula.

14. The surgical robot system of claim 1, further comprising a master unit comprising a force indicator configured to enable the radial force acting on the terminal of the surgical instrument to be perceived.

15. The surgical robot system of claim 14, wherein the force indicator is a master manipulator provided with a motor communicatively connected to the computing unit, or the force indicator is an imaging system.

* * * * *